United States Patent
Yao et al.

(10) Patent No.: US 11,052,153 B2
(45) Date of Patent: Jul. 6, 2021

(54) HIGHLY BRANCHED ALPHA-D-GLUCANS

(71) Applicant: Purdue Research Foundation, West Lafayette, IN (US)

(72) Inventors: Yuan Yao, West Lafayette, IN (US); Jingmin Joanne Zhang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 50 days.

(21) Appl. No.: 16/153,893

(22) Filed: Oct. 8, 2018

(65) Prior Publication Data

US 2019/0038753 A1 Feb. 7, 2019

Related U.S. Application Data

(63) Continuation of application No. 14/395,200, filed as application No. PCT/US2013/037365 on Apr. 19, 2013, now Pat. No. 10,117,937.

(60) Provisional application No. 61/635,453, filed on Apr. 19, 2012.

(51) Int. Cl.
| | |
|---|---|
| *A61K 47/36* | (2006.01) |
| *A61K 8/73* | (2006.01) |
| *A61Q 19/00* | (2006.01) |
| *A61K 31/192* | (2006.01) |
| *A61K 31/343* | (2006.01) |
| *C08B 37/00* | (2006.01) |

(52) U.S. Cl.
CPC ............... *A61K 47/36* (2013.01); *A61K 8/73* (2013.01); *A61K 31/192* (2013.01); *A61K 31/343* (2013.01); *A61Q 19/00* (2013.01); *C08B 37/0009* (2013.01); *A61K 2800/49* (2013.01); *A61K 2800/544* (2013.01)

(58) Field of Classification Search
CPC .. A61K 8/732; A61K 47/36; A61K 2800/544; A61K 9/5161; A61K 2800/49; A61K 9/1652; A61K 31/716; A61Q 19/00; C08B 37/0009
See application file for complete search history.

(56) References Cited

U.S. PATENT DOCUMENTS

| | | | |
|---|---|---|---|
| 2005/0013914 A1* | 1/2005 | Oku | A23L 27/70 426/544 |
| 2007/0298085 A1* | 12/2007 | Lestage | A61K 8/02 424/443 |
| 2011/0269849 A1* | 11/2011 | Yao | 514/773 |

FOREIGN PATENT DOCUMENTS

| | | |
|---|---|---|
| JP | 2012-505243 | 3/2012 |
| WO | WO2011/155505 | 12/2011 |

OTHER PUBLICATIONS

Bi et al: "Designing carbohydrate nanoparticles for prolonged efficacy of antimicrobial peptide", Journal of Controlled Release, vol. 150, 2011, pp. 150-156.

* cited by examiner

*Primary Examiner* — Johann R Richter
*Assistant Examiner* — Danielle Sullivan
(74) *Attorney, Agent, or Firm* — Woodard, Emhardt, Henry, Reeves & Wagner, LLP (57) ABSTRACT

Compositions including a highly branched alpha-D-glucan or modified forms thereof and a solute compound are described herein. The compositions can provide increased water solubility and/or increased rate of dissolution for the solute compound. The compositions can also provide increased stability for the solute compound. Methods for preparing and using compositions including a solute compound and a highly branched alpha-D-glucan are also described.

19 Claims, 8 Drawing Sheets

HIGHLY BRANCHED ALPHA-D-GLUCANS

CROSS-REFERENCE TO RELATED APPLICATIONS

The present application is a continuation of 35 U.S.C. § 371 national phase application Ser. No. 14/395,200, filed on Oct. 17, 2014, which claims the priority benefit of International Application No. PCT/US2013/037365, filed Apr. 19, 2013, which claims the priority benefit of U.S. Provisional Patent Application No. 61/635,453, filed Apr. 19, 2012, the contents of which are hereby incorporated by reference in their entirety into the present disclosure.

STATEMENT OF GOVERNMENT SUPPORT

This invention was made with government support under grant DMR1006301 awarded by the National Science Foundation. The government has certain rights in the invention.

TECHNICAL FIELD

The present disclosure relates generally to compositions for increasing the solubility and stability of solute compounds therein, and more particularly to compositions including highly branched polysaccharides that may be used to improve solubility, stability, and/or bioavailability of solute compounds for the food, nutraceutical, personal care, skin care, cosmetics, pharmaceuticals, medical, paint and coating, and agricultural industries.

BACKGROUND

In industries such as food, feed, agriculture, drug, animal drug, personal care, skin care, etc., the use of certain ingredients or extracts is difficult since their constituent materials have low or poor solubility in water, which leads to low stability, accessibility, availability, or bioavailability. Examples of such ingredients, synthetic compounds, or extracts can include phenolic compounds (e.g., flavonoids, curcuminoids), carotenoids and active pharmaceutical ingredients (APIs, e.g., drugs), as well as raw or purified extracts from herbs, microbes and animals.

One particular example of such ingredients or extracts includes phenolic compounds, such as quercetin and curcumin. Quercetin and curcumin are strong antioxidants and have anti-inflammatory, antiviral, and anti-cancer effects. In particular, curcumin is a potent anti-cancer drug that can be used clinically. However, their low solubility prohibits their use in food, nutraceutical, cosmetic, and medical formulations. To address this problem, a variety of techniques have been employed to improve the water-solubility of such low or non-soluble phenolic compounds. For example, it has been proposed to improve the solubility of curcumin using specific compounds (e.g., piperine), polymeric nanoparticle encapsulation, or surfactant micelles to disperse curcumin and improve its solubility. However, these methods are expensive and/or have limited capability to solubilize phenolic compounds. In addition, some of these strategies are simply ineffective.

Poor water solubility of some active pharmaceutical ingredients (APIs), such as a number of drugs is one of the major problems in drug formulation and drug absorption. Systems to improve the water solubility of these drugs are essential for their bioavailability. For example, application of paclitaxel in cancer therapy has been limited by its low water solubility, and current practice of dissolving paclitaxel usually leads to short-term physical stability with quick precipitation of drug molecules. To enhance paclitaxel solubility and physical stability, hydrotropes have been used to complex with drug molecules. To be effective, however, the concentration of hydrotropes needs to be very high, which may lead to difficulties in formulation and administration.

Another example is ibuprofen. Ibuprofen is a nonsteroidal anti-inflammatory drug (NSAID), and a core medicine in the WHO Model List of Essential Medicines. It is broadly used to relieve symptoms of arthritis and fever and as an analgesic where there is an inflammatory component and dysmenorrhea. Ibuprofen belongs to Biopharmaceutics Classification System (BCS) class II, for which the rate of drug dissolution or drug solubility is the rate-limiting step in the absorption.

Another example is Griseofulvin. Griseofulvin is a widely used antifungal drug in the treatment of mycotic diseases of skin, hair and nails. Griseofulvin is poorly soluble in water and has been used as a standard in the research to increase drug bioavailability.

Similar issues persist in industries related to the extraction and formulation of medicinal, nutritional, or functional materials from plant, microbial, or animal organisms, such as herbal extracts, Chinese medicine, and colorants. In such industries, there are a number of extraction processes, including: (1) aqueous extraction; (2) solvent-based extraction and (3) supercritical fluid extraction. In many circumstances, the solute compound (or materials) has low water solubility, which makes it difficult to formulate as a product. Additionally, in industries related to feed, animal drugs, personal care, cosmetics, paints, pesticides, herbicides, or other food and non-food areas, the low solubility of certain materials in products is the source of numerous difficulties in formulation, processing and/or the function of such products.

SUMMARY

Compositions for increasing the solubility and stability of solute compounds are described herein. More particularly, compositions including highly branched alpha-D-glucans that may be used to improve the solubility, stability, and/or bioavailability of solute compounds for the food, nutraceutical, personal care, skin care, cosmetics, pharmaceuticals, medical, paint and coating, and agricultural industries are described.

The inventors have surprisingly discovered that highly branched alpha-D-glucans, such as phytoglycogen (and modified forms thereof) can be used to significantly increase the solubility of a variety of relatively water-insoluble compounds such as some phenolic compounds (e.g., quercetin and curcumin), or drugs, such as ibuprophen, griseofulvin, etc. The inventors have also discovered that the compositions formed by the highly branched alpha-D-glucans and the solute compound are more stable than without highly branched alpha-D-glucans under normal storage conditions. The highly branched alpha-D-glucans therefore serve to: (1) stabilize the solute compound, e.g., stabilize the amorphous state of active pharmaceutical ingredient (API) in the solid dispersion, so when meeting with water the solute can be released to form supersaturated solution (in which case a complex between the solute compound and the highly branched alpha-D-glucan in water is not necessarily formed); and (2) to form a soluble complex of the solute compound and the highly branched alpha-D-glucan, so the solubility of the complex affects the overall solubility of drug.

BRIEF DESCRIPTION OF THE FIGURES

The present invention may be more readily understood by reference to the following drawings, wherein:

FIG. 6 is a graph showing the content of organized (crystallized) structure of ibuprofen before and after PG complexation. FIG. 6B: X-ray powder diffraction crystallograms. The sample labels are shared between Figure A and B. PG: native PG; PG-D: PG treated with DMSO (dissolving followed by solvent removal); Ibu: non-treated ibuprofen; Ibu-D: ibuprofen treated with DMSO (dissolving followed by solvent removal); 1/3: DMSO-mediated complexation of ibuprofen (1 part) with PG (3 parts); 1/3 PM-D: physical mixture between DMSO-treated ibuprofen (1 part) and PG (3 parts); 1/3 PM: physical mixture between non-treated ibuprofen (1 part) and PG (3 parts); 1/5: DMSO-mediated complexation of ibuprofen (1 part) with PG (5 parts); 1/5 PM: physical mixture between non-treated ibuprofen (1 part) and PG (3 parts).

FIG. 7 is a graph showing the improvement of curcumin solubility and in vitro permeability.

An aqueous solution, as used herein, is any solution in which water is the main solvent. The aqueous solution can include other solvents, and one or more additional solutes, while still remaining an aqueous solution. Examples of aqueous solutions include buffered solutions, salt water, drinks such as coffee, tea, beer, wine, and fruit juice, vinegar, etc. An aqueous solution can also be a phase of an emulsion (e.g. cream, lotion), a colloid, a suspension, or aerosol.

Solubility, as used herein, refers to the ability of a solute compound to dissolve in a liquid solvent to form a homogeneous solution of the solute in the solvent. The solubility of solute compound can vary depending on a number of factors, such as the temperature, pressure and the pH of the solution. Increased solubility, as used herein, refers to the ability for an increased amount of a solute to dissolve in an aqueous solution of a given composition at a given set of conditions. The extent of the solubility of a substance in a specific solvent is measured as the kinetically stable concentration, where adding more solute does not increase the concentration of the solution and begin to precipitate the excess amount of solute. Solubility is commonly expressed as a concentration.

Compositions for increasing the solubility of a solute compound are described herein. The composition includes a highly branched alpha-D-glucan and a solute compound. The solute compound exhibits improved properties when in the presence of the highly branched alpha-D-glucan, such as increased solubility, increased rate of dissolution, increased stability, and/or increased membrane permeability. While other ingredients can be present in some embodiments, such as a pharmaceutical carrier, the primary compound essential to increase the solubility of the solute compounds is the highly branched alpha-D-glucan (e.g., phytoglycogen).

Highly Branched Alpha-D-Glucans

The term "highly branched alpha-D-glucan" (highly branched $\alpha$-D-glucan), as used herein, refers to a highly branched polysaccharide formed from alpha-D-glucose molecules, such as glycogen, phytoglycogen, amylopectin, or modified forms thereof. In some embodiments, the polysaccharides are linked by alpha-D-1,4 and alpha-D-1,6 glucosidic linkages. However, in other embodiments, chemical modification (e.g., pyrodextrinization) can be used to provide highly branched alpha-D-glucans including other types of linkages, such as alpha-D-1,2 and alpha-D-1,3 linkages. The highly branched alpha-D-glucan can be obtained, derived, or extracted from a plant material, a microbe (e.g., bacterium), or a human or non-human animal, or synthesized from glucose, glucans, or other materials. In one example, the highly branched alpha-D-glucan comprises glycogen, phytoglycogen, amylopectin, and/or modified forms thereof, such as with modifications with octenyl succinate (OS) or polyethylene glycol (PEG).

As used herein, a highly branched polysaccharide is a polysaccharide having a branch density of at least about 4%. In some embodiments, the branch density of the highly branched alpha-D-glucans can range from about 5% to about 30%. In other embodiments, the branch density is at least 5%, at least 6%, at least 7%, or at least 8%. In other embodiments, the branch density can range for example, between about 7% to about 16%. For example, the branch density of amylopectin can be about 4%-6%, and the branch density of glycogen and phytoglycogen can be about 8%-11%. For example, for glucans that contain only alpha-D-1,4 and alpha-D-1,6 glucosidic linkages, branch density can be determined by comparing the number of alpha-D-1,4 and alpha-D-1,6 glucosidic linkages as follows: percentage branch density=the number of alpha-D-1,6 glucosidic linkages/(the number of alpha-D-1,4 glucosidic linkages+the number of alpha-D-1,6 glucosidic linkages)*100. In general, branch density is the percentage of branching points based on all glucosidic linkages in the glucan molecule.

In some embodiments, the highly branched alpha-D-glucan has a dendritic structure. In a dendritic structure, the polysaccharide chains are organized globularly like branches of a tree originating from a central location that acts as a primer at the core of the structure.

The branch density of the branched alpha-D-glucan can be determined by a number of methods, such as reducing end analysis, NMR, and chromatographic analysis. See Shin et al., Journal of Agricultural and Food Chemistry, 56: 10879-10886 (2008); Yao et al., Plant Physiology, 136: 3515-3523 (2004); and Yun and Matheson, Carbohydrate Research, 243: 307-321 (1993. Enzymatic treatment can affect the branch density by creating or cleaving alpha-D-1,4-glucosidic linkages and/or alpha-D-1,6-glucosidic linkages. These enzymes can be alpha-amylase, beta-amylase, debranching enzymes (e.g., pullulanase and isoamylase), transglucosidase, amyloglucosidase, and the like. Other approaches, such as acid or alkaline treatment, as well as oxidation can also affect the branch density of alpha-D-glucans. In one example, the highly branched alpha-D-glucan can be a single type of highly branched alpha-D-glucan. Alternately, the highly branched alpha-D-glucan can be a mixture that includes a plurality of different highly branched alpha-D-glucans.

In some embodiments, the alpha-D-glucan is a phytoglycogen. Phytoglycogen is a water-soluble, glycogen-like alpha-D-glucan generated by plants. One of the largest sources of phytoglycogen is the kernel of the maize mutant sugary-1 (su1), a major genotype of sweet corn. The su1 mutation leads to the deficiency of SU1, an isoamylase-type starch debranching enzyme (DBE) (James et al., Plant Cell, 7: 417-429 (1995)). In the biosynthesis of starch, starch synthase, starch branching enzyme and DBE work coordinately to produce starch granules (Yao, "Biosynthesis of starch," Comprehensive Glycoscience, edited by Hans Kamerling. Elsevier (2007)). The primary role of DBE is to trim abnormal branches that inhibit the formation of starch crystals and granules. See Myers et al. Plant Physiology, 122: 989-997 (2000) and Nakamura, Plant and Cell Physiology, 43: 718-725 (2002). In the absence of DBE, the highly branched phytoglycogen is formed to replace starch granules. Most particles range around 40-50 nm.

Each phytoglycogen particle contains hundreds or thousands of glucan chains forming a highly packed structure. The highly branched structure of phytoglycogen results in its unusually high molecular density in dispersion. In rice, the dispersed molecular density of PG is over 10 times that of starch (Wong et al., Journal of Cereal Science, 37: 139-149 (2003)). The molecular density of PG from maize is around 1198 g/mol·nm$^3$ compared with about 62 g/mol·nm$^3$ for amylopectin of starch (Huang & Yao, Carbohydrate Polymers, 83, 1665-1671 (2011)). High density renders structural integrity of PG and allows for dense grafting of functional groups. While not fully understood, it is likely that the phytoglycogen nanoparticles grow from the non-reducing ends of glucan chains at the surface by periodic branching and elongation of chains.

In some embodiments, the highly branched alpha-D-glucan is a modified highly branched alpha-D-glucan. A modified highly branched alpha-D-glucan is a highly branched alpha-D-glucan that has been modified by using chemical approaches, enzymatic approaches, physical approaches, biological approaches, or a combination of above. The highly branched alpha-D-glucan can be modified to have a different electrical charge, different hydrophobicity, an altered molecular weight, increased or decreased side chain length, a chemical or biochemical functional group, a reduced or increased branch density, altered particle size, or a combination thereof.

In some embodiments the modified highly branched alpha-D-glucan can be modified to include functional groups selected from acetate, phosphate, octenyl succinate, succinate, hydroxypropyl, hydroxyethyl, cationic groups such as those containing quaternary ammonium cations (e.g. formed using 2,3-epoxypropyl trimethylammonium chloride, EPTAC, and (3-chloro-2-hydroxypropyl) trimethylammonium chloride, CHPTAC), carboxymethyl, polyethylene glycol (PEG, or polyethylene oxide), polypropylene glycol (or polypropylene oxide), or a combination of above.

In some embodiments, the highly branched alpha-D-glucan can also be modified by bleaching, acid hydrolysis, oxidation, pyrodextrinization, or a combination of above.

In some embodiments, the highly branched alpha-D-glucan can also be treated by shear force, high pressure processing, homogenization, hydrothermal processing, microwave, radiation, dry heating, or a combination of above.

In some embodiments, the highly branched alpha-D-glucan can also be treated by conjugating with bioactive or functional groups or ligands such as antibody, antigen, aptamer, protein, peptide, amino acid, cyclodextrin, saccharide, lipid, nucleic acid and nucleotide, dendrimer, enzyme, fluorescent group or dye, magnetic group, metal ion, metal nanoparticle, quantum dot, polymer and block co-polymer, radioactive group, or a combination of above.

In some embodiments, highly branched alpha-D-glucans can be modified by enzymes such as alpha-amylase, beta-amylase, debranching enzymes (e.g., pullulanase and isoamylase), transglucosidase, amyloglucosidase, protease, and the like, or a combination of above.

In some embodiments, modification of highly branched alpha-D-glucans can be performed by using a combination of enzymatic, physical, chemical, biological, or other methods mentioned above. Modified highly branched alpha-D-glucans can have different solubility characteristics, such as increased solubility in non-aqueous solvents such as ethanol, and can have solubility, the rate of dissolution, and/or other properties associated with its environment, such as pH, ionic strength, temperature, biological environment, presence of magnetic field or various types of radiation, or a combination of above.

Solute Compounds

In one aspect, the invention described herein provides compositions for increasing the solubility of a solute compound. It should be noted that the term "solute compound" is used herein as a convenient label, but that the highly branched alpha-D-glucans can be used for purposes other than increasing solubility, such as the physical, chemical, or physicochemical stability of the solute compound. Physical stability includes the stability of a solute compound in terms of its amorphous form, crystal size, crystalline structure or form (e.g. polymorphs), or a combination thereof. Chemical stability includes the stability of a solute compound in terms of its resistance to oxidation, reduction, chemical reaction, structure change or degradation, or a combination thereof. Physicochemical stability includes physical stability, chemical stability, or a combination thereof.

A wide variety of different solute compounds can be used. While not intending to be bound by theory, it is believed that the highly branched alpha-D-glucans (and modified forms thereof) increase the solubility of the solute compounds as a result of the solute compounds becoming associated or embedded in the highly branched chains of the alpha-D-glucan, and that the solubility of these compounds then develops a character more like that of the highly branched alpha-D-glucan in which they are suspended rather than the solubility of the compounds when standing alone. Because solute compounds having substantially different hydrophobicity can become embedded within the structure of the highly branched alpha-D-glucans, the invention is particularly useful for increasing the aqueous solubility of hydrophobic or lipophilic compounds, and in particular bioactive hydrophobic compounds. Many bioactive compounds are highly hydrophobic, meaning that they are likely to be soluble in lipids (oils) and some organic solvents, while being substantially insoluble in aqueous solution. The lack of solubility of bioactive compounds in aqueous solution is an important factor limiting their therapeutic application.

In another aspect, some solute compounds, such as griseofulvin, have strong crystalline structure. The thermodynamically stable crystalline structure drives quick transformation of amorphous form of compounds toward crystallization, leading to a low stability of amorphous form. When these compounds are associated with highly branched alpha-D-glucan or it derivatives, the rate of crystallization can be reduced. This will contribute to the increased stability and solubility of the solute compounds. In other cases, some solute compounds are easy to be oxidized or degraded, such as lemon oil and vitamin E. When these compounds are associated with highly branched alpha-D-glucan or its modified forms, the rate of oxidation can be reduced.

In general, the solute compound can include any one or combination of materials for which their improved solubility or the rate of dissolution in an aqueous solution (e.g., water) is desirable. Due to their low solubility or low rate of dissolution in water, these compounds have limited accessibility and bioavailability when used alone. The compositions of the method can therefore include at least one solute compound having a water solubility and/or rate of dissolution that is greater than the water solubility and/or rate of dissolution of the solute compound in the absence of the highly branched alpha-D-glucan or the modified form thereof. In some instances, the solute compound can be a compound or a mixture of compounds selected from the group consisting of nutrients, vitamins, drugs, coloring agent, agrochemicals, pesticides, herbicides, anti-oxidants, coloring agents, hormones, essential oils, extracts from plants, Chinese medicine, animals or microbial organisms, and combinations thereof.

Solute compounds can be categorized in a variety of different manners. In some instances, the highly branched alpha-D-glucans or the modified forms thereof can be used together with relatively large solute compounds having a size from about 10,000 daltons to about 100,000 daltons. In other embodiments, the solute compound has a molecular weight or average molecular weight less than about 10,000 Daltons. In further embodiments, the solute compound has a molecular weight or average molecular weight of less than about 1,000 daltons. In other embodiments, the solute compound is a bioactive hydrophobic compound. Examples of hydrophobic compounds include phytochemicals, carotenoids, extracts from plants, animals, or microorganisms, and drugs.

Phytochemicals include phenolic compounds such as catechins, curcumin, quercetin, rutin, resveratrol, genistein, daidzein, and kaempferol; and carotenoids, e.g., lycopene, beta-carotene, and lutein.

Extracts from plant, animals, or microbial organisms (e.g., dietary supplements or medical extracts), include extracts from grape seeds, pomegranate, olive leaves, Turmeric, green tea, black tea, cocoa (cacao), insects, crustaceans, yeast, fungus, mushrooms, *ginseng*, cloves, Purslane, *Acanthopanax, rubescens, Pueraria, Ganoderma lucidum, Alisma*, Medlar, *Angelica, Gardenia*, Honeysuckle, *Sophora japonica, flavescens, Schisandra, Cassia* seed, *Salvia, Radix*, Epimedium, Licorice, *Bupleurum, Pulsatilla, Houttuynia, Coptis, Artemisia annua, Scutellaria, Codonopsis, Forsythia, Camptotheca acuminate*, and *Andrographis paniculata*.

The solute compounds of the invention can be an active pharmaceutical ingredient (e.g., a drug) such as a hydrophobic drug that is otherwise difficult to administer. Drugs include antineoplastic agents, such as paclitaxel, sagopilone, docetaxel, rapamycin, doxorubicin, daunorubicin, idarubicin, epirubicin, capecitabine, mitomycin c, amsacrine, busulfan, tretinoin, etoposide, chlorambucil, chlormethine, melphalan, and benzylphenylurea compounds; steroidal compounds, such as natural and synthetic steroids, and steroid derivatives, such as cyclopamine; antiviral agents, such as aciclovir, indinavir, lamivudine, stavudine, nevirapine, ritonavir, ganciclovir, saquinavir, lopinavir, and nelfinavir; antifungal agents, such as itraconazole, ketoconazole, miconazole, oxiconazole, sertaconazole, amphotericin b, and griseofulvin; antibacterial agents, such as quinolones, e.g., ciprofloxacin, ofloxacin, moxifloxacin, methoxyfloxacin, pefloxacin, norfloxacin, sparfloxacin, temafloxacin, levofloxacin, lomefloxacin, and cinoxacin; antibacterial agents, such as penicillins, e.g., cloxacillin, benzylpenicillin, and phenylmethoxypenicillin; antibacterial agents, such as aminoglycosides, e.g., erythromycin and other macrolides; antitubercular agents, such as rifampicin and rifapentine; and anti-inflammatory agents such as ibuprofen, indomethacin, ketoprofen, naproxen, oxaprozin, piroxicam, and sulindac.

In some embodiments, the solute compounds are active pharmaceutical ingredients with low or poor water solubility, such as acetaminophen, acetazolamide, albendazole, amiodarone, amphotericin, atorvastatin, azithromycin, azathioprine, bicalutamide, carbamazepine, carvedilol, cefdinir, cefprozil, celecoxib, chlorpromazine, chlorothiazide, cisapride, clarithromycin, clofazamine, clopidogrel, colistin, cyclosporine, cyproterone, danazol, dapsone, diclofenac, diflunisal, diloxanide, efavirenz, ezetimibe, fenofibrate, flurbiprofen, furosemide, glibenclamide, glimepiride, glipizide, glyburide, griseofulvin, haloperidol, hydrochlorothiazide, hydroxyzine pamoate, ibuprofen, imatinib mesylate, irbesartan, isotretinoin, indinavir, indomethacin, itraconazole, ivermectin, ketoconazole, ketoprofen, lansoprazole, lamotrigine, linezolid, lopinavir, lovastatin, loratadine, medroxyprogesterone acetate, meloxicam, metaxalone, methylphenidate hydrochloride, modafinil, moxifloxacin hydrochloride, mycophenolate mofetil, mebendazole, mefloquin, nalidixic acid, naproxen, neomycin, nevirapine, nelfinavir, nifedipine, niclosamide, nystatin, ofloxacin, olanzapine, oxcarbazepine, oxycodone hydrochloride, oxaprozin, orlistat, phenazopyridine, phenytoin, piroxicam, praziquantel, pioglitazone hydrochloride, pyrantel, quetiapine, raloxifene, retinol, rifampin, risperidone, ritonavir, rofecoxib, saquinavir, simvastatin, sirolimus, spironolactone, sulfamethoxazole, sulfasalazine, tacrolimus, tamoxifen, telmisartan, talinolol, terfenadine, trimethoprim, valdecoxib, valsartan, valproic acid, and warfarin.

In some embodiments, the solute compounds are cell culture components, including but not limited to one or more of following compounds: 6,7-ADTN HBr, R(−)-N-Allyl-norapomorphine HBr, p-Aminoclonidine HCl, (±)-p-Aminoglutethimide, R(+)-Atenolol, S(−) Atenolol, Butaclamol, Chloramphenicol, 4'-Chlordiazepam, Chlorthalidone, CNQX, Codeine sulfate, CV-1808, 8-Cylclopentyl-1,3-p-sulfophenylxanthine, Dexamethasone, Diazepam, Digoxin, 7,9-Dimethyluric acid, 7,9-Dimethylxanthine, 3,5-Dinitro-catechol, 1,3-Dipropyl-8-p-sulfophenylxanthine, DNQX, (S)-ENBA, Estradiol, FG-7142, Furosemide, L-Glutamic acid HCl, L-Glutamic acid diethyl ester HCl, Glutethimide, Haloperidol, Hexahydro-sila-difenidol HCl, Hexahydro-sila-difenidol HCl, p-fluoro analog, Hydrocortisone, 6-Hydroxydopamine HBr, 3-Hydroxymethyl-ß-carboline, Indomethacin, Iodotubercidin, Isobutylmethylxanthine, (−)-MDO-NPA HCl, Methotrexate, 2-Methylthio ATP, Naltrindole HCl, Quabain, Papaverine HCl, 2-Phenylaminoadeno sine, R(−)-PIA, S(+)-PIA, Pirenperone, Prochlorperazine, Progesterone, DL(±)-Propranolol, (−)-Quisqualic acid, Ranitidine HCl, Ro 15-4513, Ro 20-1724, PDE inhibitor, Ro 41-0960, COMT inhibitor, Ryanodine, SKF-83566 HCl, Spiperone HCl, Sulpride, Testosterone, Tetrahydrocannabinol, Veratridine, Vitamin A, Vitamin D.

In some embodiments, the solute compound is a phenolic compound. Phenolic compound are substances that have one or more aromatic rings and bear one or more hydroxyl substituents on the ring, including functional derivatives such as esters, methyl ethers, glycosides and other derivatives that are apparent to those skilled in the art. Included in the definition of phenolics are polyphenols having complex substitution patterns, compounds having condensed rings, and phenolics containing one or more amine moieties and/or carboxylic acid moieties. Examples of naturally occurring phenolic compounds include, but are not limited to: bergaptol, caffeic acid, capsaicin, coumarin, daidzein, 2,5-dihydroxybenzoic acid, ferulic acid, flavonoids, glycitein (isoflavone), 4-hydroxycinnamic acid, 4-hydroxycoumarin, isopimpinellin, resveratrol, synapic acid, vanillic acid, and vanillin.

Synthetic and naturally-occurring phenolic moieties, some of which may contain amine groups, carboxylic acid groups, or aminoacids, are part of many drugs. Examples of these medicinal phenolic compounds include acenocoumarol, acetarsol, actinoquinol, adrenalone, alibendol, amino salicylic acids, amodiaquine, anethole, balsalazide, bamethan, benserazide, bentiromide, benzarone, benzquinamide, bevantolol, bifluranol, buclosamide, bupheniode, chlorobiocin, chlorotrianisene, chloroxylenol, cianidanol, cinepazide, cinitapride, cinepazide, cinmetacin, clebopride, clemastine, clioquinol, coumermycin Al, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoumacetate, etilefrine, etiroxate, exalamide, exifone, fendosal, fenoldopam mesilate, fenoterol, fenoxedil, fenticlor, flopropione, floredil, fluorescein, folescutol, formoterol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indometacin, ipriflavone, isoetarine, isoprenaline, isoxsuprine, itopride hydrochloride, ketobemidone, khellin, labetalol, lactylphenetidin, levodopa, levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxoline, norfenefrine, normolaxol, novobiocin, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theodrenaline, tioclomarol, tioxolone, .alpha.-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, xamoterol.

In other embodiments, the solute compounds can be essential oils as crude or purified extracts of plants, individual compounds or their mixtures, and/or their corresponding synthetic substances. For example, thymol is a component of thyme oil. The essential oils can be *agar* oil, ajwain oil, *angelica* root oil, *anise* oil, *asafoetida*, balsam oil, basil oil, bay oil, bergamot oil, black pepper essential oil, birch, camphor, *cannabis* flower essential oil, caraway oil, cardamom seed oil, carrot seed oil, cedarwood oil, chamomile oil, *calamus* root oil, cinnamon oil, *Cistus* species, *citronella* oil, clary sage, clove leaf oil, coffee, coriander, costmary oil, *Costus* root, cranberry seed oil, cubeb, cumin oil/black seed oil, cypress, cypriol, curry leaf, *Davana* oil, dill oil, elecampane, *Eucalyptus* oil, fennel seed oil, fenugreek oil, fir, frankincense oil, galangal, *Galbanum, Geranium* oil, ginger oil, goldenrod, grapefruit oil, henna oil, *Helichrysum*, hickory nut oil, horseradish oil, hyssop, idaho tansy, jasmine oil, juniper berry oil, *Laurus nobilis*, lavender oil, *Ledum*, lemon oil, lemongrass, lime, *Litsea cubeba* oil, mandarin, marjoram, *Melaleuca* see tea tree oil, *Melissa* oil (lemon balm), *Mentha arvensis* oil/mint oil, mountain savory, mugwort oil, mustard oil, myrrh oil, myrtle, neem oil, neroli, nutmeg, orange oil, oregano oil, *orris* oil, palo *santo*, parsley oil, patchouli oil, *Perilla* essential oil, peppermint oil, petitgrain, pine oil, *Ravensara*, red cedar, roman chamomile, rose oil, rosehip oil, rosemary oil, rosewood oil, sage oil, sandalwood oil, *Sassafras* oil, savory oil, *Schisandra* oil, spearmint oil, spikenard, spruce oil, star *anise* oil, tangerine, tarragon oil, tea tree oil, thyme oil, *Tsuga*, turmeric, *valerian*, vetiver oil, western red cedar, wintergreen, yarrow oil, ylang-ylang, zedoary.

In a preferred embodiment, the solute compound is a bioactive hydrophobic compound selected from one or more of a carotenoid, a curcuminoid, a flavonoid, a sterol, a phytosterol, a saponin, an aglycone, or an algycone of a saponin (i.e., a sapogenin). In a further embodiment, the solute compound can be selected from the group consisting of curcumin, quercetin, resveratrol, thymol, paclitaxel, ibuprophen, and griseofulvin.

In some embodiments, the solute compounds are hydrophobic vitamins, such as Vitamin A, Vitamin E, Vitamin D, and Vitamin K.

In some embodiments, the solute compounds are hydrophobic colorants, such as carotenoids, lutein, carmine, turmeric, cacao, annatto (bixin), paprika, hematoxylin, anthocyanins, lac dye, chlorophyllin, cochineal, lycopene.

In some embodiments, the compositions of the present invention show increased solubility in water and allow the preparation of aqueous solutions of a wide variety of concentrations. As the concentrated solutions can be diluted with an aqueous medium in any proportion and over a wide range of pH conditions without separation or precipitation of the hydrophobic compound, the solubility of the compound is maintained under physiological conditions, for example after an oral or parenteral administration of the composition. This normally results in an improved bioavailability of the solute compound.

The soluble compositions of the present invention can be easily incorporated into pharmaceutical, nutraceutical, medical, or cosmetic formulations in which the solute compound shows improved bioavailability. Such formulations may further contain additional active ingredients and/or a pharmaceutically or cosmetically acceptable additives or vehicles, including solvents, surfactants, adjuvants, texture agents, bulking agents, excipients, sweeteners, fillers, colorants, flavoring agents, lubricants, binders, moisturizing agents, preservatives and mixtures thereof. Collectively, these additional formulation materials can be referred to as the pharmaceutically acceptable carrier. "Pharmaceutically acceptable" as used herein means that the carrier is suitable for administration to a subject for the methods described herein, without unduly deleterious side effects. The formulations may have a form suitable for a topical (e.g., a cream, lotion, gel, ointment, dermal adhesive patch), oral (e.g., a capsule, tablet, caplet, granulate, powder, liquid), or parenteral (e.g., suppository, sterile solution) administration. Among the acceptable vehicles and solvents that may be employed for administration by injection are water, mildly acidified water, Ringer's solution and isotonic sodium chloride solution.

In other embodiments, the soluble compositions including a solute compound and a highly branched alpha-D-glucan can be incorporated into other types of formulations. Examples of these additional formulations include foods and beverages, food supplements, cell culture, agrochemicals such as fertilizers and pesticides, paint and coating, and the like. The formulation of such nutritional, agricultural, or chemical formulations is known to those skilled in the art.

Compositions including bioactive hydrophobic compounds according to the present invention may be administered to a warm-blooded animal, particularly a human, in need of the prophylaxis or therapy. The dose of a bioactive hydrophobic compound and the corresponding dose of its soluble composition together with the highly branched alpha-D-glucan (or modified forms thereof) for treating diseases or disorders will vary upon the manner of administration, the age, sex, the body weight of the subject, and the condition being treated, and will be ultimately decided by the attending physician or veterinarian. Such an amount of the bioactive compound in the form of its water-soluble composition as determined by the attending physician or veterinarian is referred to herein as a "therapeutically effective amount".

The mass ratio of solute compound to highly branched alpha-D-glucan can vary from about 100:1 to about 1:1000. The ratio of solute compound to highly branched alpha-D-glucan can vary depending on the type of composition being provided. For example, in compositions intended to stabilize a solute compound in dry form, a mass ratio ranging from about 100:1 to about 1:50 of solute compound to highly branched alpha-D-glucan can be used, with a mass ratio ranging from about 2:1 to about 1:20 being preferred. Alternately, in compositions for increasing the solubility of solute compound, a lower ratio of solute compound to highly branched alpha-D-glucan can be used. For example, for a soluble composition, a mass ratio ranging from about 1:1 to about 1:1000 of solute compound to alpha-D-glucan can be used, with a mass ratio ranging from about 1:5 to about 1:50 being preferred. The lower limit of the mass ratio is not critical, and the highly branched alpha-D-glucan can be used in any excess. However, this is not desirable in some applications, since increasing the amount of the highly branched alpha-D-glucan decreases the concentration of the active ingredient in the composition and in its aqueous solutions.

Use of Highly Branched Alpha-D-Glucan to Increase Solubility, Rate of Dissolution, and/or Stability Combination of the highly branched alpha-D-glucan or modified forms thereof with the solute compound provides a variety of benefits. In some embodiments, the invention provides a method of increasing the solubility, the rate of dissolution, and/or stability of a solute compound by combining the solute compound with an effective amount of the highly branched alpha-D-glucan.

The present disclosure provides a method of increasing the solubility and/or the rate of dissolution of a solute compound. The method includes the steps of combining an effective amount of at least one highly branched alpha-D-glucan, or a modified form thereof, with a solvent, combining the solute compound with a second solvent, and adding the two together. In some embodiments, the solute compound and the highly branched alpha-D-glucan are first combined, and are then added to the solvent. However, the method need not follow the order in which these steps are described. In other words, in some embodiments, it may be preferable to add the solute compound to a solvent, and then add the highly branched alpha-D-glucan. The increased solubility is exhibited once the solute compound has been placed together with the highly branched alpha-D-glucan, in a process that involves the use of a solvent or no solvent. The solvent can be a relatively polar solvent, and in some embodiments is an aqueous solvent (e.g., water), and in some embodiments is a mixture of aqueous and non-aqueous solvent. As described herein, addition of the highly branched alpha-D-glucan to the solute compound results in the solute compound becoming associated or enmeshed in the branches of the alpha-D-glucan so that the solute compound is solubilized along with the highly branched alpha-D-glucan.

In some embodiments, to achieve enhanced solubility and/or rate of dissolution of solute compounds, a solvent is not necessary for combining a solute compound with a highly branched alpha-D-glucan or its modified form, since this highly branched alpha-D-glucan or its modified form can interact, dissolve, or adsorb solute compounds without the use of a solvent. The processing for such a non-solvent combination can be assisted with extrusion, pressing, homogenization, grinding, rolling, kneading, ultra-sonication, or a combination of above.

Use of the highly branched alpha-D-glucan (e.g., phytoglycogen) or its modified forms to increase the solubility of solute compounds can increase the solubility of the solute compounds to a varying degree, depending on the particulars of the solute compound, the highly branched alpha-D-glucan or its modified forms, and the solution in which the solute compound is placed. For example, in some embodiments the method increases the solubility of the solute compound by at least about a factor of two relative to the solubility of the solute compound in the absence of the highly branched alpha-D-glucan. In other words, in some instances, the solute compound can have a solubility that is at least two times greater than the solubility of the solute compound in the absence of a highly branched alpha-D-glucan. In other instances, the solute compound can have a solubility that is at least five times greater than the solubility of the solute compound in the absence of a highly branched alpha-D-glucan. In further instances, the solute compound can have a water solubility that is at least ten times greater than the solubility of the solute compound in the absence of the highly branched alpha-D-glucan, and in yet further embodiments, the solubility of the solute compound is at least one hundred times greater when combined with the highly branched alpha-D-glucan.

Phenolic compounds are one type of solute compound whose solubility is significantly enhanced by highly branched alpha-D-glucans or their modified forms. The present invention is capable of increasing the solubility of some phenolic compounds by at least ten times compared with their solubility in the absence of the highly branched alpha-D-glucans. For example, use of phytoglycogen can increase the solubility of curcumin in aqueous solution by at least 100 times, and can increase the solubility of quercetin in aqueous solution by at least 10 times.

In other embodiments, a method of increasing the stability of a solute compound is provided. The method includes the steps of adding an effective amount of at least one highly branched alpha-D-glucan, or a modified form thereof, to the solute compound and combining the solute compound with a solvent. As with the methods for increasing solubility, the steps of this method can be carried out in any order. The solute compound complexed with the highly branched alpha-D-glucan or its modified forms thereof is more resistant to crystallization, oxidation, reduction, structure change, deterioration and degradation, enzyme reaction, chemical reaction, or a combination thereof, than the solute compound in the absence of a highly branched alpha-D-glucan. In addition, because crystallization lowers the solubility and/or rate of dissolution of solute compounds, stabilization of the solute compounds in a non-crystallized form improves solubility and/or rate of dissolution. Compositions including a solute compound and the highly branched alpha-D-glucan show an excellent stability over long periods of time, in one embodiment, for over a month in room temperature, in another embodiment, for over one year.

In some embodiments, for enhanced stability of solute compounds, a solvent may not be necessary for combining a solute compound with a highly branched alpha-D-glucan or its modified form, since this highly branched alpha-D-glucan or its modified form can interact, dissolve, or adsorb solute compounds without the use of a solvent. The processing for such a non-solvent combination can be extrusion, pressing, homogenization, grinding, rolling, kneading, ultra-sonication, or a combination of above.

Figure 5:
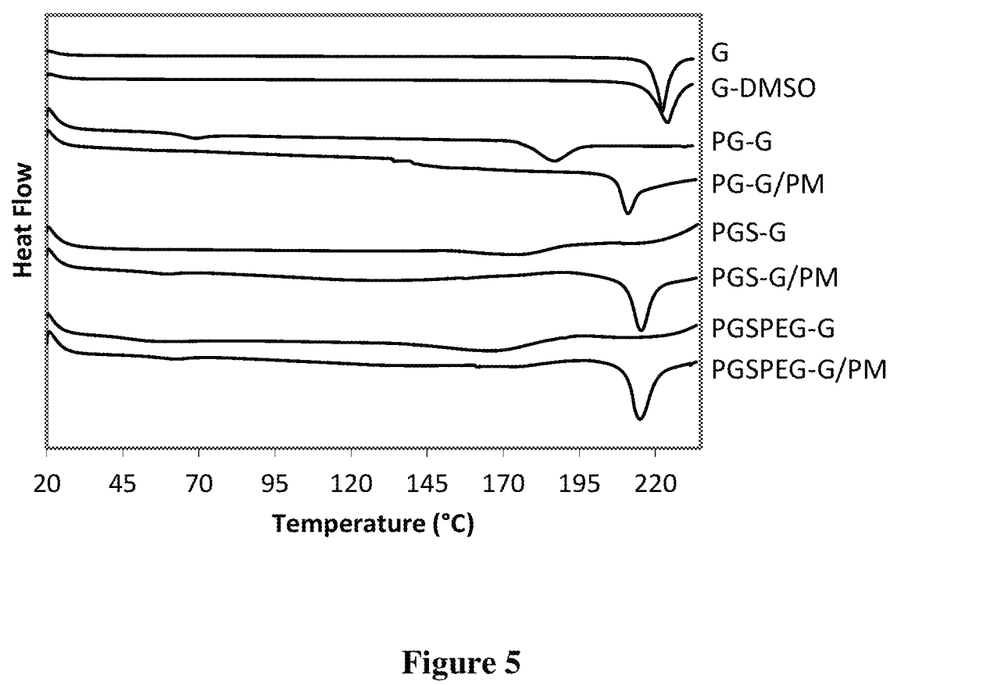
FIG. 5 is a graph showing the normalized DSC curves of griseofulvin in various systems. G: griseofulvin. G-DMSO: griseofulvin dissolved in DMSO followed by solvent removal. PG-G, PGS-G, and PGSPEG-G: griseofulvin complexed with native PG, PG-succinate (PG-S), and PG-succinate-PEG (PG-S-PEG), respectively using DMSO as solvent followed by solvent removal. These complexes were placed at 22° C. for 37 days before DSC tests. PG-G/PM, PGS-G/PM, and PGSPEG-G/PM: griseofulvin physically mixed with native PG, PG-S, and PG-S-PEG, respectively using mortar and pestle. For all mixtures, the griseofulvin/carrier ratio was 1/3 (w/w).

FIG. 5 shows that modified forms of phytoglycogen can stabilize the amorphous (or near amorphous) form of griseofulvin from transformation to crystalline structure. The ratio of solute compound (griseofulvin) to modified forms of phytoglycogen in this figure is 1/3 (w/w). When placed in contact with an aqueous system (in the GI tract, for example), the amorphous drug will form a supersaturated solution and to realize higher permeation in the time scale of absorption.

Preparation of Compositions Including the Solute Compound and the Highly Branched Alpha-D-Glucan or the Modified Forms Thereof Another aspect of the invention involves methods for preparing a soluble composition. In one embodiment, the method includes dissolving the solute compound in a solvent to form a solution; mixing the solution with the highly branched alpha-D-glucan, or a modified form thereof; and removing the solvent to obtain the soluble composition. In some embodiments, the solvent is a mixture of non-aqueous solvent and aqueous solvent.

In another embodiment, the method for preparing a soluble composition includes the steps of dissolving or dispersing at least one solute compound in a first solvent to form a first solution or dispersion; dissolving or dispersing at least one highly branched alpha-D-glucan or a modified form thereof in a second solvent to form a second solution or dispersion; mixing the first and second solutions or dispersions together to form a mixture; and removing the solvent from the mixture to obtain a composition; wherein the water solubility of the solute compound in the composition is greater than the water solubility of the solute compound in the absence of the at least one highly branched alpha-D-glucan or a modified form thereof. In some embodiments, the first solvent can be an aqueous solvent; in some embodiments, the first solvent can be a non-aqueous solvent; in some embodiments, the first solvent can include a mixture of non-aqueous solvent and an aqueous solvent. In further embodiments, the second solvent can be an aqueous solvent; in some embodiments, the second solvent can be a non-aqueous solvent; in some embodiments, the second solvent can include a mixture of a non-aqueous solvent and an aqueous solvent.

In other embodiment, the method for preparing a solute composition includes the steps combining at least one solute compound with at least one highly branched alpha-D-glucan or a modified form thereof. The combination can be in a solvent, or without any solvent.

In some embodiments, the solvent is a non-aqueous solvent. Examples of non-aqueous solvents can be selected from the group consisting of pentane, cyclopentane, hexane, cyclohexane; benzene; toluene; 1,4-dioxane, chloroform, diethyl ether, dichloromethane, tetrahydrofuran, ethyl acetate, acetone, dimethylformamide, acetonitrile, dimethyl sulfoxide, formic acid, n-butanol, isopropanol, n-propanol, ethanol, methanol, acetic acid, and combinations thereof. In some embodiments, the solvent can be a non-aqueous solvent. In some embodiments, the solvent can include a mixture of non-aqueous solvent and an aqueous solvent.

In some embodiments, the soluble composition including the solute compound and the highly branched alpha-D-glucan or a modified form thereof can be prepared with additional processing steps. For example, in some embodiments, the highly branched alpha-D-glucan is derived or extracted from a plant source, an animal source, or a microbial source, or synthesized, or a combination thereof. In additional embodiments, preparation of the soluble composition further includes the step of processing the mixture by kneading, extrusion, homogenization, ultrasonic, high-pressure treatment, high-speed treatment, microwave treatment, radiation treatment, heat treatment, or a combination thereof. In yet further embodiments, the method includes removing the solvent from the mixture by spray drying, vacuum drying, freeze drying, drum drying, heat drying, extrusion, supercritical extraction, or a combination thereof.

When combining solute compounds with highly branched alpha-D-glucans, it can sometimes be challenging to find a single solvent in which both carrier and solute compound are soluble. DMSO is a particularly effective solvent in this regard, but it can be difficult to remove DMSO after complexation. In these situations, it may be preferable to prepare a modified form of the highly branched alpha-D-glucan that is soluble in ethanol, acetone, or this type of low polar or non-polar solvent. For example, phytoglycogen has been modified into phytoglycogen octenyl succinate (PG-OS), which can be dissolved in non- or low-polarity solvents. To further improve the solubility of alpha-D-glucan, polyethylene glycol (PEG) chains can be added on PG-OS, thus generating PG-OS-PEG. This new material has much enhanced solubility than PG-OS.

In some embodiments, a solvent is not necessary for combining a solute compound with a highly branched alpha-D-glucan or its modified form, since this highly branched alpha-D-glucan or its modified form can interact, dissolve, or adsorb solute compounds without the use of a solvent. The processing for such a non-solvent combination can be assisted with blending, extrusion, pressing, tableting, homogenization, grinding, rolling, kneading, ultra-sonication, or a combination of above.

The present invention is illustrated by the following examples. It is to be understood that the particular examples, materials, amounts, and procedures are to be interpreted broadly in accordance with the scope and spirit of the invention as set forth herein.

EXAMPLES

Example 1: Use of Phytoglycogen and PG-OS to Increase Solubility of Quercetin and Curcumin Matured kernels of su1-containing sweet corn were used to extract phytoglycogen. Quercetin and curcumin were purchased from Sigma-Aldrich (St. Louis, Mo.) and used without further purification. The stock solutions of quercetin (7 mg/mL) and curcumin (4.25 mg/mL) were prepared in ethanol and stored in amber bottles in the dark at 4° C. Other chemicals used were of analytical reagent grade. Deionized water was used throughout.

Extraction of Phytoglycogen

Sweet corn kernels were ground into grits and then mixed with 4 to 6 weights of deionized water. The suspension was homogenized using a high-speed blender (Waring Laboratory, Torrington, Conn.), and then centrifuged at 8000×g for 20 min. The supernatant was collected whereas the solid was further extracted twice using deionized water. Thereafter, the supernatant at each batch was combined and passed through a 270-mesh sieve. The liquid was then added to ethanol to precipitate the polysaccharide. After centrifugation and decanting the supernatant, the precipitate was re-dispersed by ethanol and centrifuged. The suspension after the last ethanol addition was filtered to remove excess liquid. The solid was placed in the fume hood to remove residual ethanol. The powder collected contains phytoglycogen.

Preparation of Phytoglycogen Octenyl Succinate (PG-OS)

To the suspension of phytoglycogen, 1-octenyl succinic anhydride was added. The pH was maintained between 8.5 and 9.0 using NaOH. The reaction was terminated after 24 hours by reducing pH to 6.5 using HCl. To collect substituted glucans, three volumes of ethanol were added to the reaction mixture. The precipitates were collected and further dehydrated using 3 cycles of ethanol suspension-centrifugation. The solid collected after filtration was placed in a fume hood to remove residual ethanol.

Mixing Quercetin or Curcumin with Phytoglycogen

Aqueous dispersions 10 ml of phytoglycogen were prepared at 0.1, 0.5, 1.0, and 5.0% in $Na_2HPO_4$-citric acid buffer (pH 6.6) and filled in a screw-capped tube. A 0.1 mL aliquot of the quercetin or curcumin stock solution was added to phytoglycogen dispersions, which is followed by agitation for 2 hours at 22° C. Thereafter, insoluble quercetin or curcumin was removed by centrifugation.

Quantification of Quercetin by Capillary Electrophoresis (CE)

The concentration of quercetin in aqueous system was determined using CE. The CE experiments were carried out with a Beckman instrument MDQ P/ACE (Palo Alto, Calif., USA) equipped with a spectrophotometric detector. The separations were performed with an uncoated fused-silica capillary (47.0 cm×50 μm ID×375 μm OD) obtained from Polymicro Technologies (Phoenix, Ariz., USA). The temperature of the capillary was maintained at 25° C. UV detection was performed at 254 nm. Running buffer of 0.05 M borate (pH 9.0) was used. The applied voltage was 20 kV of positive polarity. All the samples including standard solutions were filtered through 0.45 μm syringe filters. Mobility measurements were done in triplicate. The Beckman 32 karat software (version 7.0) was used for peak area quantifications.

Spectrophotometric Determination of Curcumin

Curcumin-phytoglycogen mixture was added to ethanol to precipitate the polysaccharide and extract curcumin. After centrifugation, the supernatant was measured with a UV-Vis spectrophotometer (Varian Instruments, Walnut Creek, Calif.). The absorbance of the solution was measured at 425 nm against a reagent blank which was prepared with the same reagent concentration but without curcumin. The standard curve was prepared using solutions of 1.0-8.0 μg/ml curcumin in 80% ethanol.

Increased Solubility of Quercetin Using Phytoglycogen

Figure 1:
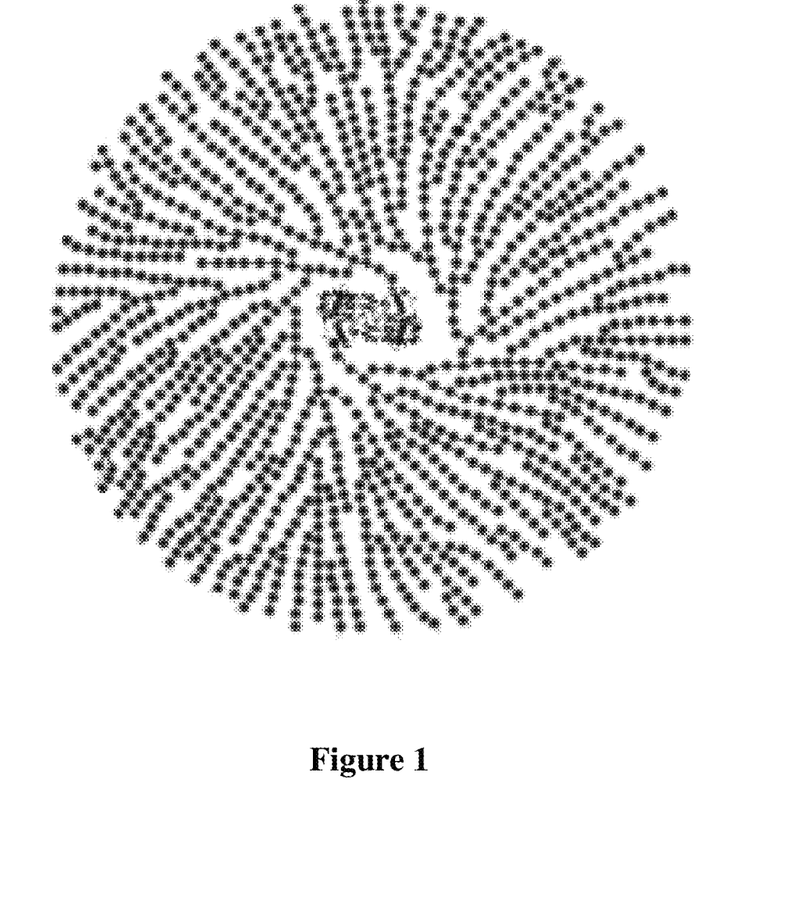
FIG. 1 is a schematic representation of glycogen showing the dendritic structure of this molecule.
Figure 2:
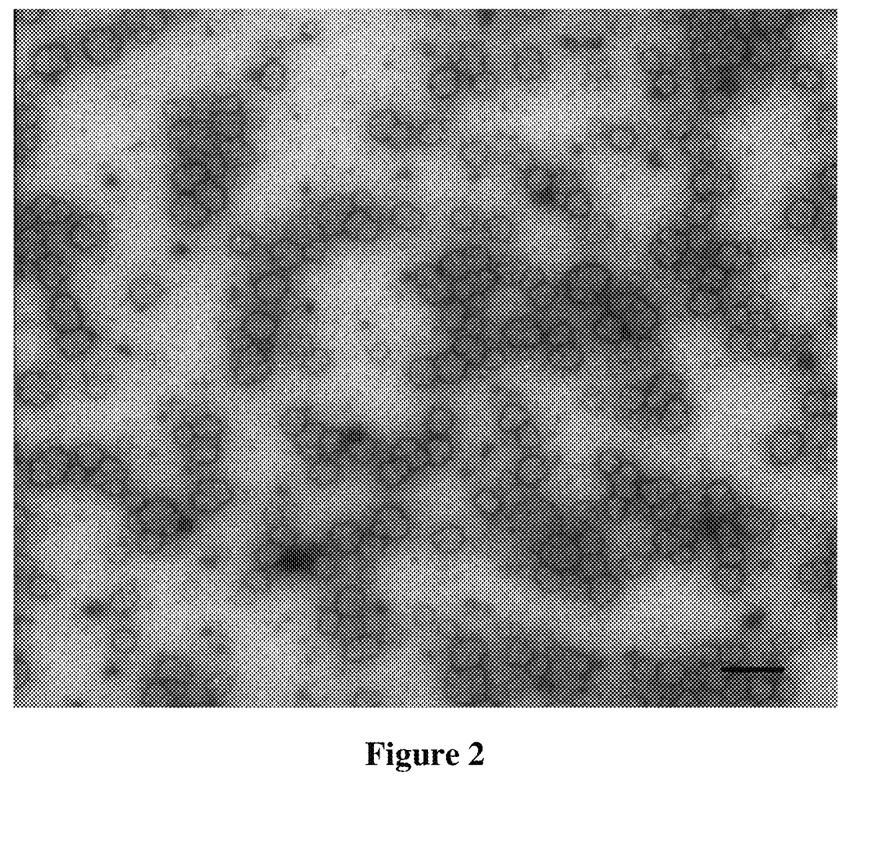
FIG. 2 is a transmission electron microscopy (TEM) image of phytoglycogen nanoparticles.
Figure 3:
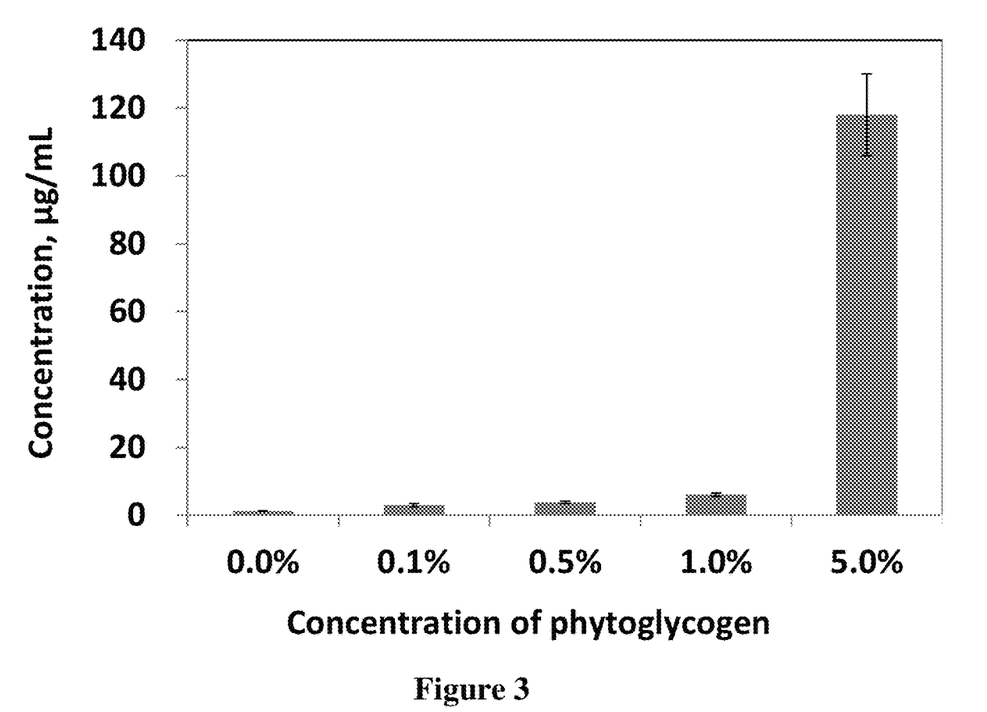
FIG. 3 is a graph showing that the solubility of quercetin is affected by phytoglycogen concentration at 22° C. and pH 6.6.

FIG. 3 shows the solubility of quercetin in various concentrations of phytoglycogen dispersion. Significant increase in quercetin solubility was found with increased concentration of phytoglycogen. Compared with quercetin alone (0.0% phytoglycogen), the use of 1.0 and 5.0% phytoglycogen increased quercetin solubility by around 5.0 and 97.4 times, respectively.

Increased Solubility of Curcumin Using Phytoglycogen and PG-OS

Figure 4:
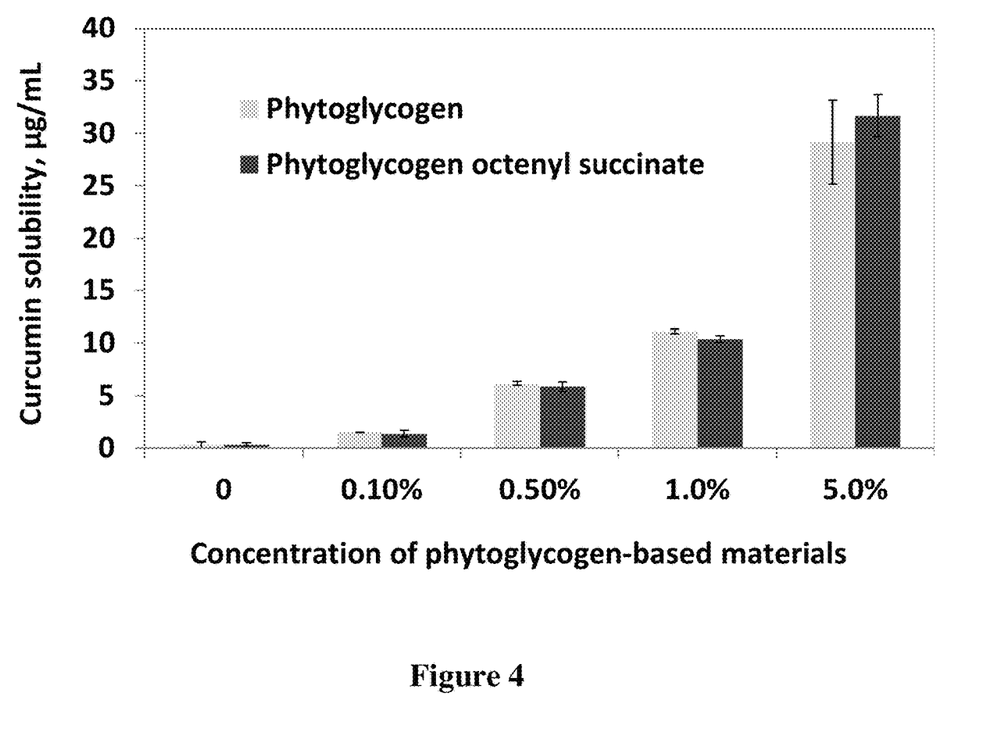
FIG. 4 is a graph showing that the solubility of curcumin is affected by the concentration of phytoglycogen and phytoglycogen octenyl succinate (PG-OS) at 22° C. and pH 6.6.

The solubility of curcumin in various concentrations of phytoglycogen was shown in FIG. 4. Estimated water solubility of curcumin was reported to be 11.0 ng/mL (Kaminaga et al. Letters, 555, 311-316 (2003)). In our test, the solubility of curcumin was below the detection limit (0.30 μg/mL). A significant increase in curcumin solubility was found as the concentration of phytoglycogen or PG-OS increased. For example, the solubility of curcumin was 29.1 and 31.8 μg/mL for 5.0% phytoglycogen and PG-OS dispersion respectively, which was nearly 3,000 times higher than the reported value of curcumin alone.

Example 2: Preparation of Phytoglycogen Octenyl Succinate (PG-OS) and PEGylated Phytoglycogen Octenyl Succinate (PG-OS-PEG)

Three grams of phytoglycogen and 5.85 grams octenyl succinic anhydride (OSA) was mixed in 15.0 mL of dimethyl sulfoxide (DMSO) and then transferred in 50-mL tube. The tube was placed in a boiling water bath for 3 hours for the reaction. Thereafter, the reactant was separated into two portions. One half was used for preparing PG-OS-PEG, and another half was used to isolate PG-OS. To isolate PG-OS, the reaction was stopped by adding 20 times deionized water, and the liquid was neutralized to pH 6.5 using NaOH solution. The liquid was then subjected to ultrafiltration process.

To prepare PG-OS-PEG, to another half PG-OS reactant, 30.6 grams of poly(ethylene glycol) methyl ether (average $M_n$ 550, mPEG-OH) was added. The mixture was maintained at 110° C. with vacuum, with agitation for every 15 minutes for 15 hours. Thereafter, the reactant was diluted by 20 times deionized water, and the liquid was neutralized to pH 6.5 using NaOH solution. The liquid was then subjected to ultrafiltration process.

For both diluted and neutralized PG-OS and PG-OS-PEG reactants, the ultrafiltration was conducted using a Minimate™ tangential flow filtration system (Pall Life Sciences). The ultrafiltration was conducted 4 cycles, and for each cycle the volume of retentate was reduced to 1/20 of the original and then added with deionized water back to original volume. The final retentate was subjected to freeze drying to collect solid PG-OS and PG-OS-PEG.

Example 3: Complexation of PG-OS and PG-OS-PEG with Curcumin to Improve Curcumin Solubility In 14-mL tubes, 30 mg PG-OS, PG-OS-PEG, β-cyclodextrin (βCD), and hydroxypropyl β-cyclodextrin (HPβCD) were respectively mixed with 2.97 mL sodium acetate (NaAC) buffer (10 mM, pH 6.5). To each mixture, excess amount of curcumin powder was added and the mixture was treated using a high speed homogenizer (T25-DS1 Ultra-Turrax®, IKA) for 7 minutes at 22,000 rpm. Thereafter, 1.0 mL aliquot was drawn from each mixture and subjected to centrifugation. The supernatant was added to ethanol to extract curcumin. After centrifugation to remove precipitate, the supernatant was further diluted in 80% ethanol, and curcumin content was determined using a UV-Vis spectrophotometer (Varian Instruments) at 425 nm against a standard curve. Table 1 shows the solubility of curcumin when complexed with 10 mg/mL carriers. Evidently, both PG-OS and PG-OS-PEG had higher capability than βCD and HPβCD to improve the aqueous solubility of curcumin.

TABLE 1

Curcumin solubility in pH 6.5 10 mM NaAc buffer as affected by carriers

| Carrier, 10 mg/mL | Curcumin Solubility, μg/mL | Carrier/curcumin ratio, w/w |
| --- | --- | --- |
| PG-OS | 303 | 33.0/1 |
| PG-OS-PEG | 367 | 27.5/1 |
| βCD* | 45.1 | 222/1 |
| HPβCD** | 110 | 91/1 |

*βCD: β-cyclodextrin
**HPβCD: hydroxypropyl β-cyclodextrin

Example 4: Preparation of Phytoglycogen Succinate (PG-S) and PEGylated Phytoglycogen Succinate (PG-S-PEG)

To prepare PG-S, 3 grams of phytoglycogen and 3.7 grams of succinic anhydride (SA) was mixed in 15.0 mL of dimethyl sulfoxide (DMSO) and then transferred in a 50-mL tube. The tube was placed in a boiling water bath for 3 hours for the reaction. To isolate PG-S, the reaction was stopped by adding 20 times of deionized water, and the liquid was neutralized to pH 6.5 using NaOH solution. The liquid was then subjected to ultrafiltration process.

To prepare PG-S-PEG, 3 grams of phytoglycogen and 3.7 grams of succinic anhydride (SA) was mixed in 15.0 mL of dimethyl sulfoxide (DMSO) and then transferred in a 50-mL tube. The tube was placed in a boiling water bath for 3 hours for the reaction. To the PG-S reactant, 30.6 grams of Poly(ethylene glycol) methyl ether (average $M_n$ 550, mPEG-OH) was added. The mixture was maintained at 110° C. with vacuum, with agitation for every 15 minutes for 7 hours. Thereafter, the reactant was diluted by 20 times of deionized water, and the liquid was neutralized to pH 6.5 using NaOH solution. The liquid was then subjected to ultrafiltration process.

For both diluted and neutralized PG-S and PG-S-PEG reactants, the ultrafiltration was conducted using a Minimate™ tangential flow filtration system (Pall Life Sciences). The ultrafiltration was conducted 4 cycles, and for each cycle the volume of retentate was reduced to 1/20 of the original and then added with deionized water back to original volume. The final retentate was subjected to freeze drying to collect solid PG-S and PG-S-PEG.

Example 5: Complexation of PG-S and PG-S-PEG with Griseofulvin

Griseofulvin (Sigma-Aldrich) 0.55 grams, 1.65 grams PG-S or PG-S-PEG and 6.05 grams of DMSO were mixed using mortar and pestle. The mixture was transferred to glass vials and vacuum dried to completely remove DMSO. As control, griseofulvin was dissolved in DMSO in the same ratio as that for the complexation and subjected to vacuum drying to collect griseofulvin solid. In addition, physical mixtures of griseofulvin and PG-S or PG-S-PEG were prepared at a ratio of 1/3 as controls.

After 37 days at 22° C., differential scanning calorimetry (DSC) analysis was conducted for samples of griseofulvin complexed with PG-S and PG-S-PEG with several controls. For DSC analysis, materials (3-7 mg) were weighed and sealed in PerkinElmer aluminum-hermetic pans. DSC tests were conducted using DSC Q2000 (TA Instruments) with scanning rate of 20° C./min over 20-250° C. Heat flow (W/g) for each sample was normalized according to the content of griseofulvin for each sample. The results are shown in FIG. 5. Evidently, a complexation of griseofulvin with PG-S or PG-S-PEG led to negligible crystallization after 37 days of storage, showing a high stability of the amorphous form of griseofulvin.

Example 6: Reduction of Ibuprofen Crystallization by Complexation with Phytoglycogen To prepare phytoglycogen-ibuprofen complex, ibuprofen, phytoglycogen and DMSO were mixed in a ratio of 1:3:6 or 1:5:10 by weight. The resulting pastes were placed in vacuum to remove DMSO and the collected solids were ground into powder. Meanwhile, ibuprofen was treated using DMSO in a similar manner (dissolving in DMSO followed by solvent removal) and the solid collected was used in preparing several control samples. Dry mixes of phytoglycogen and original or DMSO-treated ibuprofen were prepared. These materials were used for DSC and X-ray powder diffraction analysis.

Figure 6A:
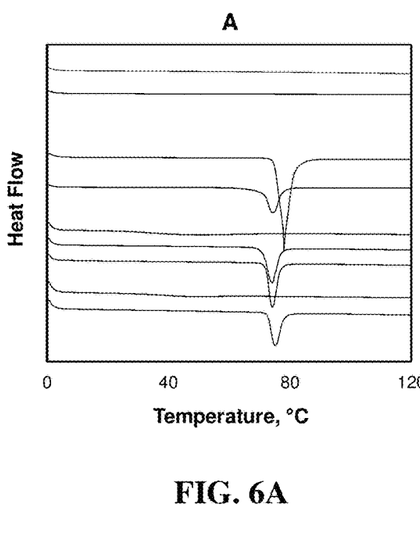
FIG. 6A: DSC heat flow curves.
Figure 6B:
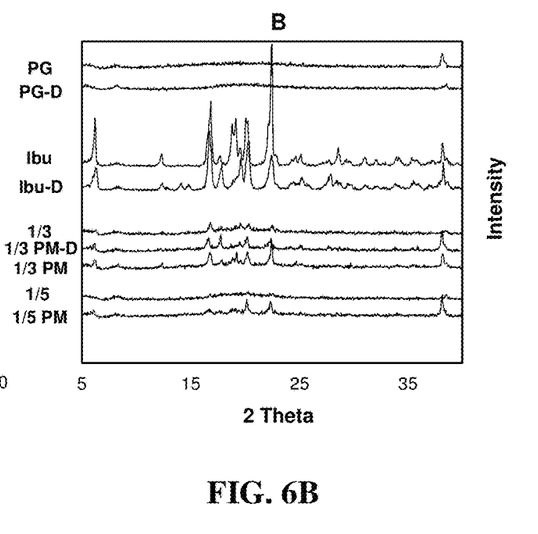

For DSC analysis, each solid were weighted and sealed into PerkinElmer aluminum-hermetic pans and subjected to DSC Q2000 (TA Instruments) with scanning rate of 20° C./min over 0 to 250° C. Each DSC curve was normalized using the weight of ibuprofen. For X-ray powder diffraction analysis. Solid powders were weighted and analyzed using Shimadzu XRD-6000 X-ray powder diffractometer equipped with a Bragg-Brentano optical setup. Samples were scanned with a step size of 0.08° from 5 to 40° 2θ. The DSC and X-ray diffraction analysis results are shown in FIG. 6. Evidently, the complexation of phytoglycogen with ibuprofen led to significantly reduced or negligible crystal amount in the ibuprofen-containing solids.

Example 7: Curcumin Solubility and Caco-2 Cell Monolayer Permeability Increased by Phytoglycogen Complexation The curcumin stock solution in ethanol was prepared by mixing 10 mg curcumin in 1.0 mL ethanol, vortexing, and centrifuging to collect supernatant. Meanwhile, 2 grams phytoglycogen was dispersed in 40 mL $Na_2HPO_4$-citric acid buffer (pH 3.0-6.6). 0.4 mL curcumin stock solution was added to phytoglycogen dispersion; the mixture was centrifuged to remove insoluble curcumin. The supernatant was collected and freeze dried to prepare phytoglycogen-curcumin complexation solid.

Figure 7A:
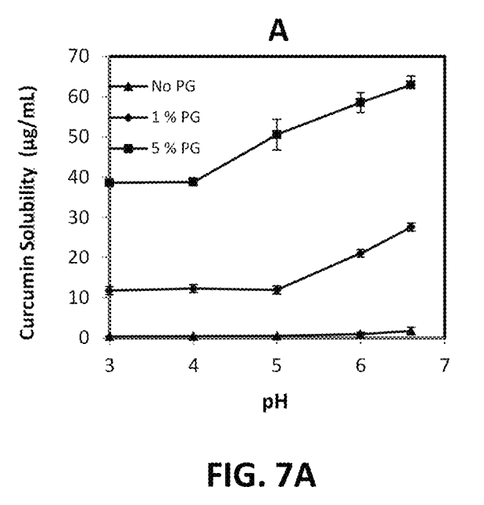
FIG. 7A shows curcumin solubility-enhancing effect of phytoglycogen (PG) in the $Na_2HPO_4$-citric acid buffer (pH3.0-6.6). No PG: no PG used, curcumin homogenized in buffer; 1% PG: dispersion of PG-curcumin complex with 1.0% PG; 5% PG: dispersion of PG-curcumin complex with 5.0% PG.

Phytoglycogen-curcumin complexation solid was dispersed in buffers to form 1% and 5% (w/v) dispersions. After centrifugation, the supernatant was added to 4 volumes of ethanol to precipitate the polysaccharide and extract curcumin. After centrifugation, the supernatant was measured with a UV-Vis spectrophotometer. The absorbance of the solution was measured at 425 nm. The quantity of curcumin was determined using a standard curve of curcumin in 80% ethanol. The results are shown in FIG. 7-A. Evidently the phytoglycogen-curcumin complexation significantly increased the solubility of curcumin in the buffer.

To conduct Caco-2 cell monolayer permeation tests, Caco-2 BBe cells originally obtained from ATCC were maintained in Dulbecco's Modified Eagle Medium (DMEM) that contains FBS (10%), sodium pyruvate, and penicillin/streptomycin at 37° C. under an atmosphere of 5% $CO_2$ and 95% air. Cells were seeded on the apical side of Transwell plate, and allowed to reach 100% confluence and to differentiate for 21 days after seeding. Transepithelial electrical resistance (TEER) value was used to determine the integrity of each cell monolayer. Fully differentiated Caco-2 BBe cells on Transwell plate were washed with Hank's Balanced Salt Solution (HBSS). In order to estimate the permeation from an apical to a basolateral compartment, 0.5 ml of HBSS that contain a curcumin preparation was added to the apical side and 1.5 ml of HBSS added to the basolateral side. Cells were incubated at 37° C. and for every 30 min, 750 µl HBSS was withdrawn from the basolateral compartment and replaced with an equal volume of fresh HBSS to maintain the volume. The amount of curcumin in the HBSS aliquots from basolateral compartment was quantified using LC-MS to evaluate the monolayer permeation.

Figure 7B:
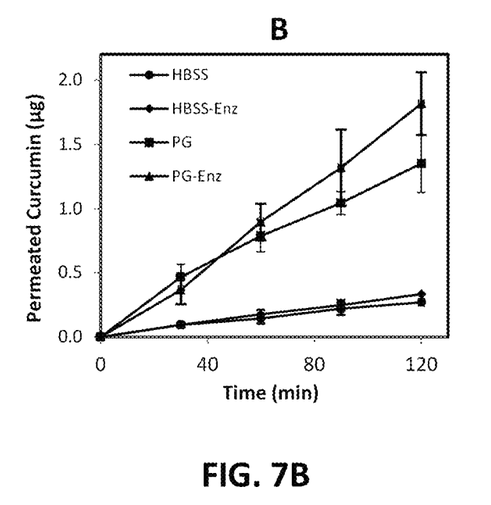
FIG. 7B shows the impacts of PG complexation and enzymes ($\alpha$-amylase and amyloglucosidase) added in the apical compartment (of Caco-2 cell monolayer model) on curcumin accumulation in the basolateral compartment. HBSS-CCM: curcumin powder homogenized in Hanks' balanced salt solution (HBSS); HBSS-CCM-Enz: curcumin powder homogenized in HBSS and then added with enzymes; PG-CCM: PG-curcumin complex in HBSS; PG-CCM-Enz: PG-curcumin complex in HBSS added with enzymes. For all tests, the starting concentration of curcumin in the apical compartment was 60 µg/mL.

Curcumin-containing buffer from the basolateral compartment was subjected to solid phase extraction using Oasis® filters (Waters). Adsorbed curcumin was eluted using acetonitrile (ACN) and dried by vacuum. The solid was then dissolved with 50 µL ACN and transferred to injection vials and then subjected to LC-MS analysis. The results are shown in FIG. 7-B. Evidently, the solubility increase of curcumin led to its increase for Caco-2 cell monolayer permeability. Importantly, the use of amylases in the apical compartment improved curcumin permeation, which indicates the impact of digesting enzymes on phytoglycogen degradation and curcumin release.

Example 8: Phytoglycogen to Solubilize Thymol to Inhibit Pathogen *Salmonella typhimurium*

Three grams of phytoglycogen and 3 grams of thymol (Sigma-Aldrich) were dispersed in sodium acetate buffer (50 mM, pH 5.5) to make 10% (w/v) for both. The mixture was subjected to high speed homogenization. After homogenization, the dispersion was centrifuged to collect aqueous liquid. The concentration of thymol in this phytoglycogen-thymol liquid stock was determined to be about 400 µg/mL. As reference, a thymol-alone stock of 400 µg/mL in sodium acetate buffer (50 mM, pH 5.5) was prepared by adding thymol in the buffer and vortex.

The phytoglycogen-thymol stock and thymol-alone stock were added to Brain Heart Infusion (BHI) broth to make the thymol concentrations of 12.5, 25, 50, 80, 100, and 125 µg/mL. To the glass tubes containing these broth liquids, *Salmonella typhimurium* culture (about $10^9$ CFU/mL) was inoculated at a 1.0% (v/v) level, and all liquids were incubated at 37° C. for 24 hours. Thereafter, the tubes were photographed for comparing the turbidity. The appearance of turbidity shows the growth of bacteria.

Figure 8:
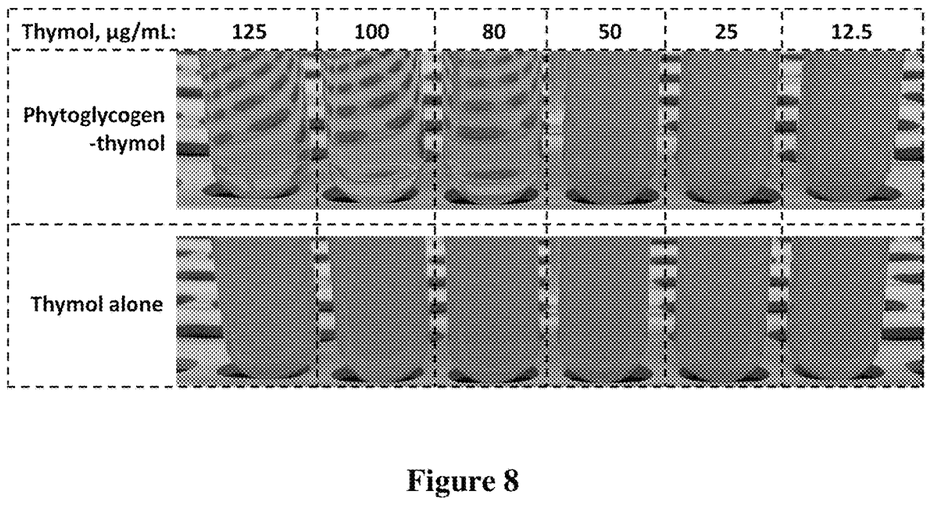
FIG. 8 provides a photograph showing detection of minimum inhibitory concentration (MIC) for thymol in phytoglycogen-thymol complex and in thymol-alone preparations. Clear and transparent liquids show negligible bacterial growth.

As shown in FIG. 8, for the BHI broth liquids added with phytoglycogen-thymol complex preparation, the minimum inhibitory concentration (MIC) of thymol was 80 µg/mL (i.e. at and above this thymol concentration the liquid was clear, showing negligible growth of bacteria). For BHI broth added with thymol-alone preparation, the MIC was not detectable even at a thymol concentration as high as 125 µg/mL. This shows that the phytoglycogen-thymol complexation improves the solubility and availability of thymol against *Salmonella*.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A modified highly branched alpha-D-glucan having greater than 4% branch density, the modified highly branched alpha-D-glucan comprising octenyl succinate, the modified highly branched alpha-D-glucan further comprising hydroxypropyl, hydroxyethyl, polyethylene glycol, polypropylene glycol, or combinations thereof.

2. The modified highly branched alpha-D-glucan according to claim 1 and further comprising at least one substitution group selected from the group consisting of antibody, antigen, aptamer, protein, peptide, amino acid, cyclodextrin, saccharide, lipid, nucleic acid and nucleotide, dendrimer, enzyme, fluorescent group or dye, magnetic group, metal ion, metal nanoparticle, quantum dot, polymer and block copolymer, radioactive group, and combinations thereof.

3. The modified highly branched alpha-D-glucan according to claim 1 prepared by at least one treatment selected from the group consisting of acid hydrolysis, oxidation, pyrodextrinization, enzymatic treatment using alpha-amylase, beta-amylase, debranching enzyme, transglucosidase, amyloglucosidase, and/or protease, bleaching, shear force treatment, extrusion, kneading, homogenization, hydrothermal processing, dry heating, microwave treatment, radiation, and combinations thereof.

4. The modified highly branched alpha-D-glucan according to claim 1 which improves a property of a solute compound, wherein the property is selected from the group consisting of the aqueous solubility, dissolution rate, and stability against crystallization, oxidation, degradation, deterioration, reduction, or structure change, and combinations thereof.

5. A composition comprising a modified highly branched alpha-D-glucan according to claim 1 and a solute compound, the composition having increased solubility and/or stability of the solute compound, wherein the mass ratio of the solute compound to the modified highly branched alpha-D-glucan is from 100:1 to 1:1000.

6. The composition according to claim 5, wherein the solute compound is an active hydrophobic compound selected from the group consisting of phytochemicals, carotenoids, extracts from plants, animals or microorganisms, and drugs.

7. The composition according to claim 5, wherein the solute compound is synthetic or naturally-occurring phenolic moieties.

8. The composition according to claim 5, wherein the solute compound is an active pharmaceutical ingredient.

9. The composition according to claim 5, wherein the solute compound is selected from the group consisting of niclosamide, ivermectin, sirolimus, indomethacin, paclitaxel, griseofulvin, ibuprofen, quercetin, curcumin and thymol.

10. The composition according to claim 5, wherein the ratio of solute compound to the modified highly branched alpha-D-glucan is about 1:3, wherein the modified highly branched alpha-D-glucan reduces the rate of amorphous-to-crystalline transforming of the solute.

11. The modified highly branched alpha-D-glucan according to claim 1 comprising octenyl succinate and hydroxypropyl.

12. The modified highly branched alpha-D-glucan according to claim 1 comprising octenyl succinate and one or more substituents selected from the group consisting of polypropylene glycol, polypropylene oxide and combinations thereof.

13. The modified highly branched alpha-D-glucan according to claim 1 comprising octenyl succinate and one or more substituents selected from the group consisting of polyethylene glycol, polyethylene oxide and combinations thereof.

14. The modified highly branched alpha-D-glucan according to claim 13 and comprising one or more additional substituents selected from the group consisting of polypropylene glycol, polypropylene oxide and combinations thereof.

15. The modified highly branched alpha-D-glucan according to claim 1 in which the modified highly branched alpha-D-glucan is a modified phytoglycogen or glycogen material.

16. The modified phytoglycogen or glycogen material of claim 15 comprising octenyl succinate and hydroxypropyl.

17. The modified phytoglycogen or glycogen material of claim 15 comprising octenyl succinate and one or more substituents selected from the group consisting of polypropylene glycol, polypropylene oxide and combinations thereof.

18. The modified phytoglycogen or glycogen material of claim 15 comprising octenyl succinate and one or more substituents selected from the group consisting of polyethylene glycol, polyethylene oxide and combinations thereof.

19. The modified phytoglycogen or glycogen material of claim 18 further comprising one or more substituents selected from the group consisting of polypropylene glycol, polypropylene oxide and combinations thereof.

* * * * *